United States Patent
Schafer et al.

(10) Patent No.: US 6,276,209 B1
(45) Date of Patent: Aug. 21, 2001

(54) SYSTEM AND METHOD OF ASSESSING THE STRUCTURAL PROPERTIES OF WOODEN MEMBERS USING ULTRASOUND

(75) Inventors: Mark E. Schafer, Ambler, PA (US); Robert J. Ross, Madison, WI (US); John R. Erickson, Madison, WI (US); Rodney C. DeGroot, Madison, WI (US)

(73) Assignees: Perceptron, Inc., Plymouth, MI (US); The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 09/466,750

(22) Filed: Dec. 17, 1999

Related U.S. Application Data

(60) Provisional application No. 60/157,182, filed on Sep. 30, 1999.

(51) Int. Cl.[7] .............................. G01N 29/08; G01N 29/18
(52) U.S. Cl. .................................. 73/597; 73/598; 73/599; 73/600
(58) Field of Search .............................. 73/597, 598, 639, 73/618, 599, 600

(56) References Cited

U.S. PATENT DOCUMENTS

| | | | |
|---|---|---|---|
| 5,143,072 | * | 9/1992 | Kantorovich et al. ................. 73/597 |
| 5,307,679 | * | 5/1994 | Ross ........................................ 73/597 |
| 6,029,522 | * | 2/2000 | Schafer et al. ........................ 73/598 |

\* cited by examiner

*Primary Examiner*—John E. Charman
(74) *Attorney, Agent, or Firm*—Woodcock Washburn Kurtz Mackiewicz & Norris LLP

(57) ABSTRACT

A system and method of detecting anomalies and/or grain variations in a wooden member. At least one ultrasonic transmitter applies an ultrasound waveform into a surface of a wooden member so as to generate a multiplicity of ultrasonic waves including, e.g., longitudinal and shear ultrasonic waves. These ultrasonic waves are measured after propagation through the wooden member by at least one ultrasonic receiver disposed on the same surface of the wooden member. At least one ultrasonic receiver may also be placed opposite the ultrasonic transmitter so as to detect radial transmission of the longitudinal ultrasonic wave at a point across from the wooden member. The received ultrasonic waves are processed to determine anomalies and/or grain variations in the wooden member at positions of the wooden member between the ultrasonic transmitter and the ultrasonic receiver(s). The ultrasonic transmitters and receivers may be placed in rollers to facilitate high-speed, in-line processing of wooden members.

9 Claims, 4 Drawing Sheets

FIG. 1
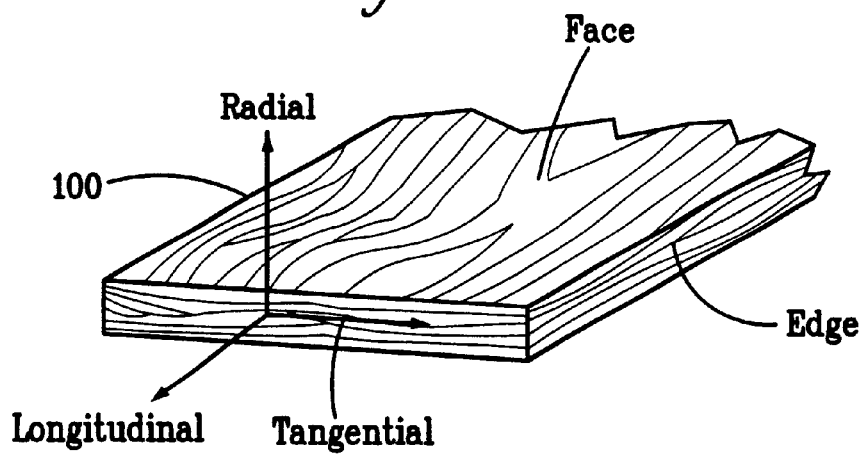
FIG. 2
Prior Art
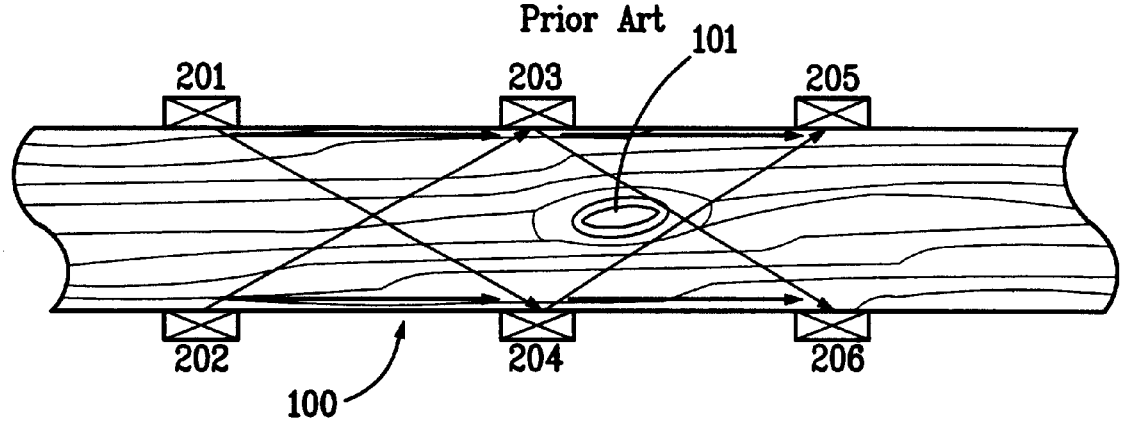
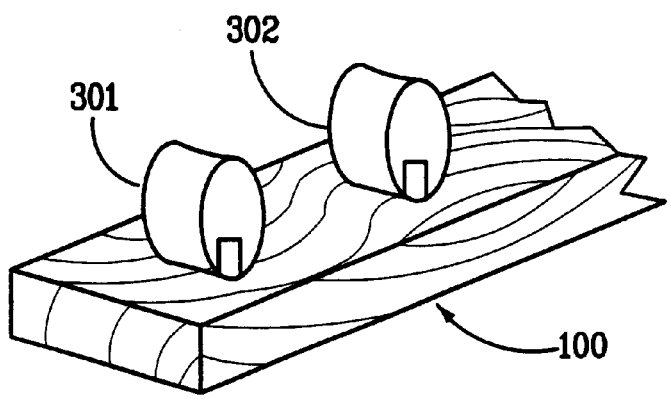
FIG. 3

SYSTEM AND METHOD OF ASSESSING THE STRUCTURAL PROPERTIES OF WOODEN MEMBERS USING ULTRASOUND

CROSS REFERENCE TO RELATED APPLICATIONS

The present application is a regular utility application claiming priority of U.S. Provisional Patent Application No. 60/157,182, filed Sept. 30, 1999 the contents of which are hereby incorporated by reference.

STATEMENT OF GOVERNMENT SUPPORT

The Invention was made by an agency of the United States Government or under a contract with an agency of the United States Government. The name of the U.S. Government agency and the Government contract number are: U.S. Department of Agriculture 98-CRADA-3162.

FIELD OF THE INVENTION

The present invention relates to a system and method for ultrasound non-destructive testing of materials such as wood. More particularly, the present invention relates to the use of ultrasound to make specific determinations regarding the material through which the ultrasound passes. For example, wood with or without defects or other characteristics of interest may be examined using the ultrasound techniques of the invention.

BACKGROUND OF THE INVENTION

FIG. 1 shows the standard orientation directions when discussing wooden members. The longitudinal direction is along the fiber orientation, that is, in the direction of the trunk of the tree. The radial direction is across all the rings and therefore across the grain. The tangential direction is traveling with the ring. There are several established methods for determining the strength of such wooden members, specifically structural "2x" material. A first method uses a bending device, referred to as a "Continuous Lumber Tester" or CLT. This device applies a fixed bending deflection to the wooden member as it passes through a series of rollers. The load presented by the member under a fixed deflection is an indication of its structural quality. A second method uses X-ray imaging to estimate the density of the material, and to image defects such as knots, which reduce the strength of the piece. A third method uses low frequency (audible) sound propagation characteristics along the length of the wooden member to determine an overall Modulus of Elasticity and damping.

The first method directly measures the bending Modulus of Elasticity (MOE) of the material and infers strength (tensile and compression), while the second method assumes that the strength is proportional to the density, which is correct to a first approximation. In fact, the Young's Modulus, or the Modulus of Elasticity, is related to the density times the square of the sound velocity. The third method employs an impact method to excite a longitudinal wave that reflects back and forth along the length of the wooden member; the time of the reflections is an indication of the sound speed, and therefore the Young's Modulus of the member. This latter approach has been previously disclosed in the prior art by Pellerin & Ross, for example.

Ultrasonic devices have also been used in the prior art to assess lumber strength. For example, the use of side mounted transducers firing in a cross pattern was disclosed in a paper by Rajeshwar et al. (B. Rajeshwary, D. Bender, D. Bray, K. McDonald, "An Ultrasonic Technique for Predicting Tensile Strength in Southern Pine Lumber", Trans. Am. Soc. Agri. Eng., 40(4):1153–1159, 1997)). FIG. 2 is an example of their transducer placement and ultrasound wave directions.

There are several drawbacks to each of the above-mentioned prior art methods. For example, the CLT uses a three point measurement system in which the load is placed at the center of the board, with supports for the board spaced 4 feet apart. Thus, for a typical 8 foot length board, only the center section is measured with any accuracy. As a result, these machines typically are followed by a manual visual inspection station, where a human operator looks for grade-limiting defects, especially in the end regions. There are obvious visual defects, such as edge knots or severe grain angles, which reduce the strength of the lumber in bending, tension, and compression. The CLT, since it measures the bending modulus, does not directly assess compressional strength along the wooden member. This is the reason that additional human grading, or "override" decision, is necessary. The CLT also has the drawback that if the wood is quite unsound it can break during the load testing. Since the wood travels through the machine at up to 1500 linear feet per minute, the broken wooden pieces can jam or otherwise maladjust the CLT, causing the entire measurement line to stop.

The X-ray Lumber Grader, or XLG, on the other hand, has the drawback that X-ray density is not completely indicative of strength. There are species and growing conditions in which the density of the wood is "normal", and yet the boards fail very quickly under load. In addition, many biological deterioration agents degrade the mechanical properties of wood yet do not change the density of wood. Thus, the data must be augmented. Several researchers have been experimenting with combining X-ray data with ultrasound measurements of sound speed to improve prediction accuracy. However, the resulting device is very complex. In addition, there is always a small risk involved in equipment that uses ionizing radiation.

The technique disclosed by Pellerin and Ross provides only an overall assessment of lumber quality, and does not properly account for the specific type and locations of defects that affect its ultimate utility as a strength member. Specifically, the location and orientation of knots, splits, and grain angle all affect the tensile and compression strength of the member, but the data from the reflected waveforms does not provide sufficient detail to account for these defects. Further, the technique disclosed by Pellerin and Ross is somewhat difficult to implement at high board feed rates, since it requires the boards to be relatively motionless while the ends are impacted and monitored. Further, there is often extraneous vibration energy in the wooden member due to machinery and handling equipment, which can cause errors in the estimation of reflected wave speeds.

The accurate grading of wooden members, for example, structural softwood lumber or hardwood pallet stock, requires that multiple characteristics of the wooden member be determined simultaneously. The overall stiffness and tensile strength of the wooden member must be measured in order to estimate the structural grade of the member. Fiber orientation, or grain angle, is also a primary determining factor in strength estimation. The location and size of defects, such as knots, splits, and decay or deterioration, also affect the structural properties of the material. Strength characteristics can be inferred from the sound propagation speed along the direction of the fibers. Therefore, the present invention is designed to provide a technique for use in identifying and measuring such characteristics while overcoming the above-mentioned limitations in the prior art so as to accurately assess the structural properties of wooden members for strength and/or quality grading purposes.

SUMMARY OF THE INVENTION

The present invention solves the afore-mentioned needs in the prior art by providing a system and method of detecting anomalies and/or grain variations in a wooden member using at least one ultrasonic transmitter that applies an ultrasound waveform into a surface of a wooden member so as to generate several wave motions, e.g., a longitudinal ultrasonic wave and a shear ultrasonic wave, which are measured after propagation through the wooden member by at least one ultrasonic receiver disposed on the same surface of the wooden member. At least one ultrasonic receiver may also be placed on the opposite side of the wooden member from the ultrasonic transmitter so as to detect ultrasonic wave motions, e.g., a longitudinal wave in the radial direction, travelling through the wooden member. The received multiplicity of waveforms are processed to determine anomalies and/or grain variations in the wooden member at positions of the wooden member between the ultrasonic transmitter and the ultrasonic receiver(s) by, for example, comparing the measured values to references values taken from a reference wooden member to determine if variations are present. In a sample configuration, a first ultrasonic receiver along the surface may receive a longitudinal ultrasonic wave and a shear ultrasonic wave, as well as other wave motions, and a second ultrasonic receiver across from the transmitter may receive a longitudinal ultrasonic wave. The outputs of the receivers may be processed to determine the variations in the longitudinal ultrasonic wave and the shear ultrasonic wave. Other wave motion combinations are possible, and key to the approach of the invention is the recognition of the anisotropic nature of the wood with regard to sound speed. This causes "mode conversion" from one type of wave motion into another, thereby enhancing the detection of defects.

In one embodiment of the invention, the ultrasonic transmitter comprises a plurality of ultrasonic transmitters in a first roller adapted to roll along the surface of the wooden member and the ultrasonic receiver comprises a plurality of ultrasonic receivers in a second roller adapted to roll along the surface of the wooden member. In such an embodiment, the multiplicity of wave motions, e.g., the longitudinal and shear ultrasonic wave components, which have traveled along different paths through the wooden member, may be measured and compared to determine the grain angle of the wooden member. In this embodiment, the individual components of the multiplicity of waveforms along different paths may be related to one another, rather than from a reference wooden member, to determine the variations.

BRIEF DESCRIPTION OF THE DRAWINGS

The present invention will be better understood after reading the following detailed description of the presently preferred embodiments thereof with reference to the appended drawings, in which:

FIG. 1 shows the standard orientation directions when discussing wooden members, where the longitudinal direction is along the fiber orientation, that is, in the direction of the trunk of the tree, the radial direction is across all the rings and therefore across the grain, and the tangential direction is traveling with the ring.

FIG. 2 is an example of a prior art ultrasonic system showing the transducer placement and ultrasound wave directions.

FIG. 3 shows a configuration of ultrasound transducers positioned on one side, specifically the top, of a wooden member, such as a piece of structural wood, or "2×" material, in a perspective view.

DETAILED DESCRIPTION OF THE PRESENTLY PREFERRED EMBODIMENTS

Figure 4:
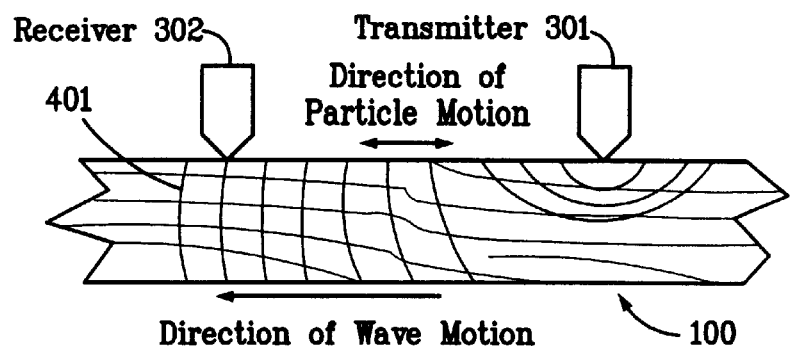
FIGS. 4 and 5 show examples of two of several possible types of wave motion generated by the ultrasound transmitter and picked up by the ultrasound receiver.

A system and method which meets the above-mentioned objects and provides other beneficial features in accordance with the presently preferred exemplary embodiment of the invention will be described below with reference to FIGS. 1–11. Those skilled in the art will readily appreciate that the description given herein with respect to those figures is for explanatory purposes only and is not intended in any way to limit the scope of the invention. Accordingly, all questions regarding the scope of the invention should be resolved by referring to the appended claims.

It is well known that the speed of sound in wood is affected by the grain orientation, in that the speed in the longitudinal direction (FIG. 1) is about 5000 meters per second (m/s), while in the radial direction, it is about 1200 m/s, and finally, in the tangential direction, it is about 1500 m/s. The strength of a wooden member, as expressed by the Young's Modulus Y, is related to the speed of sound by the following equation:

$$Y = \rho c^2$$

Thus, knowledge of the speed of sound gives a highly sensitive measure of the strength of the wooden member. Although additional knowledge of the density would provide a more complete estimate of Modulus of Elasticity ("MOE"), the density of wood does not vary as much as the sound speed, and the sound speed term is to second order, increasing its importance relative to density. Further, the two tend to track one another, so there is not a substantial increase in the accuracy when both are known. On the other hand, the X-ray systems, which detect density, have problems with wooden members in which the density is relatively constant, and the strength varies considerably. One such condition is "compression wood", which is caused by trees growing on steep hills, or in regions of constant prevailing winds in a specific direction. In these cases, the wood has different structural properties on the uphill (upwind) side and the downhill (downwind) side.

In the Rajeshwar et al. system noted above with respect to FIG. 2, strength-limiting defects were noted by waves traveling along the edges of the board. FIG. 2 shows the orientation of transducers 201, 202, 203, 204, 205, and 206 along the edges of wooden member 100. Ultrasound waves are propagated along the edges of member 100, between transducers 201 to 203, 202 to 204, 203 to 205, and 204 to 206, as shown in FIG. 2. If there were an edge knot, the signal level would drop dramatically. This system also monitored the sound speed along the signal paths from 201 to 204, 202 to 203, 203 to 206, and 204 to 205, as noted in the figure. The purpose of these measurement paths is to determine the slope of the grain of the wooden member. As explained in more detail below, the system disclosed herein improves upon and more fully explains the phenomena discussed by Rajeshwar et al.

FIG. 3 shows the orientation of two ultrasound transducers built within roller structures in order to permit rapid scanning of the wooden member as it travels longitudinally, as for instance, along a production line in accordance with the invention. The transducers 301 and 302 are both placed on the top surface of the wooden member 100 as shown. One of the transducers acts as a transmitter 301, the other as a receiver 302.

FIG. 4 shows the first of several possible wave motions that may be induced in the board 100 from the transducers 301 and 302 placed on the top surface. By specific changes to the construction of the transducers 301 and 302, it is possible to transmit and receive other wave motions including not only longitudinal but also "Rayleigh," "Love," and "Lamb" wave motions, depending upon the nature of the transducers and the orientation of the wave motion with regard to the orientation of wave speeds (grain direction) within the board 100. The incident ultrasound wave from the transmitter 301 spreads out into the board 100. Because the speed of sound along the length of the board 100 is up to 4 times faster than in the other directions, the wave is refracted in such a way that a longitudinal wave 401 progresses down the length of the board 100, even though the initial wave motion was from the top to the bottom of the board 100. This property of wave bending and subsequent longitudinal motion allows for the measurement of longitudinal properties of the board 100, such as strength.

Figure 5:
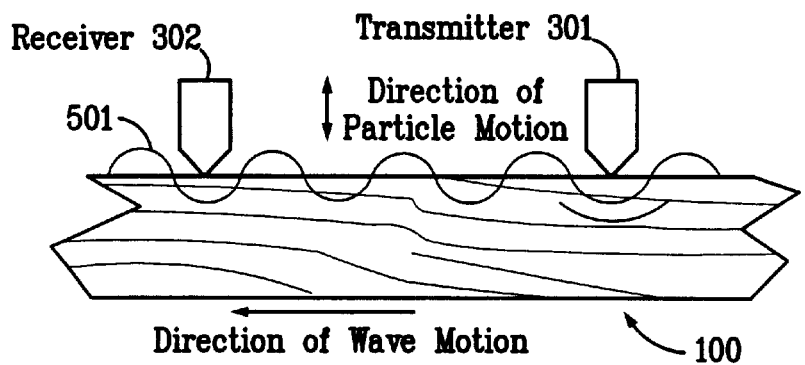

FIG. 5 depicts a second primary mode of wave motion in the board 100 induced by transducers 301 and 302 on the top surface. In this case, there is wave conversion from a longitudinal wave into a surface shear wave 501. This wave travels at a speed more related to the speed across the member, and not at the longitudinal sound speed. This wave is highly affected by surface properties and grain angles.

One of the unique aspects of the present invention is the detection of multiple combined wave motion patterns (e.g., a longitudinal and a shear wave as depicted in FIGS. 4 and 5) with a single pair of transducers. It is due in part to the use of high bandwidth and center frequency transducers, and the anisotropic nature of wood.

Figure 6:
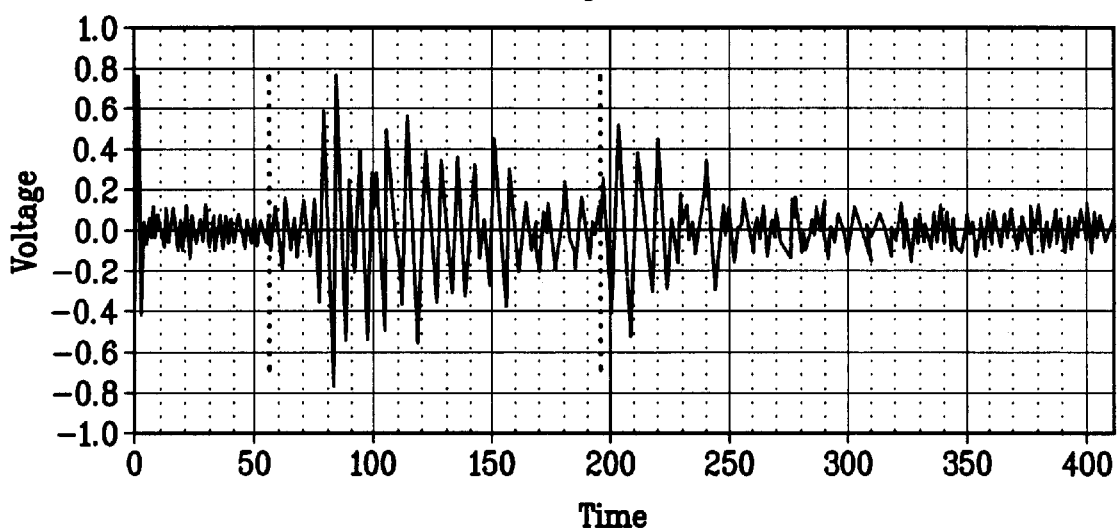
FIGS. 6 and 7 are examples of the received waveforms from the configuration of FIG. 3.
Figure 7:
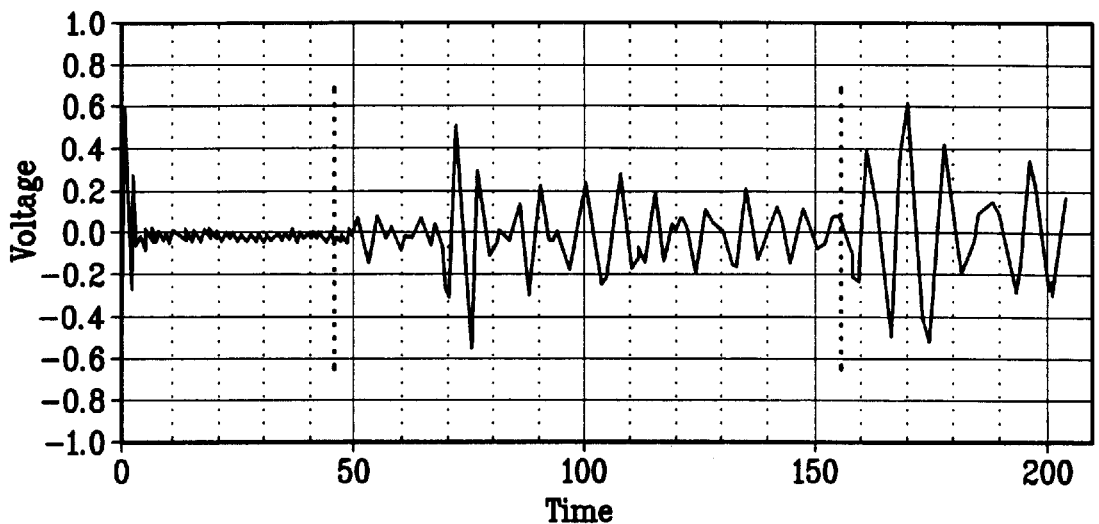

FIGS. 6 and 7 are two illustrations of an example of laboratory data taken to show this effect. The two illustrations are oscilloscope recordings using two timebase resolution settings for clarity. In FIG. 6, it is clear that there are at least two waveforms at the receiver. By changing the separation distance between the source 301 and receiver 302, the independence of the two waveforms was much more clearly shown. As the separation distance between the source 301 and receiver 302 changed, the relative positions of the two signal peaks changed, again indicating that the two signals represented two separate wave velocity components, rather than, for instance, a reflection of a single wave at some interface.

From a series of measurements at several separation distances, the wave velocities of the longitudinal and shear components were determined. As an example, the data in the table below summarize the data for one such measurement.

| Separation Distance (in/mm) | Time to 1st waveform ($\mu s$) | Time to 2nd Waveform ($\mu s$) |
| --- | --- | --- |
| 12/30.5 | 64 | 223 |
| 10/25.4 | 55 | 190 |
| 8/20.3 | 46 | 157 |

Based on this data, it can be deduced that the first wave travels with a sound speed of 5644 meters/second, and the second, slower, wave travels at a sound speed of 1539 meters/second. Referring to published literature on sound speeds in wood (V. Bucur), these sound speeds correspond to a longitudinal wave as described and a shear wave, whose sound speed is closer to that of the wave travelling from top to bottom in the wooden member. Thus, with a single measurement, two independent measurements of wood characteristics can be obtained.

Although the generation/reception of longitudinal waves from one side of the wooden member has been demonstrated in the literature before (Rajeshwar et al), those works have not recognized that a second waveform component is present within the wave. Further, no additional work has been done on defect localization as will now be described.

Figure 8:
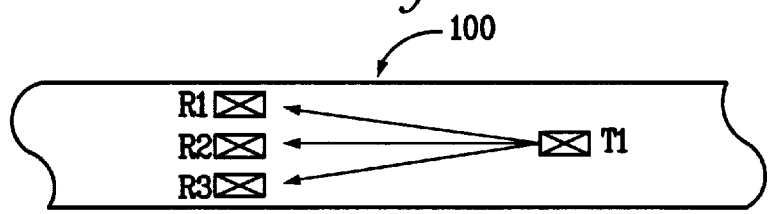
FIG. 8 shows three acoustic wave pathways from a single transmitter to three receivers and the grain orientation of the wood.

In order to further improve the quality detection capabilities, several receivers, R1, R2, R3, can be placed to receive the waves generated by a single transmitter, T1, as shown in FIG. 8. This diagram shows the paths of the ultrasound wave along the top surface of the wooden member 100 from one transmitter (T1) to several, independent receivers (R1, R2, R3). Because the speed of sound is dependent upon the orientation of the wood grain, the variation in received speed of sound at the three receivers is an indication of the relative grain orientation between the transmitter and the receivers. For example, with the grain orientation shown in the figure, the measured speed of sound between the transmitter T1 and receiver R3 would be faster than the measured speed of sound between the transmitter T1 and receiver R1.

Figure 9:
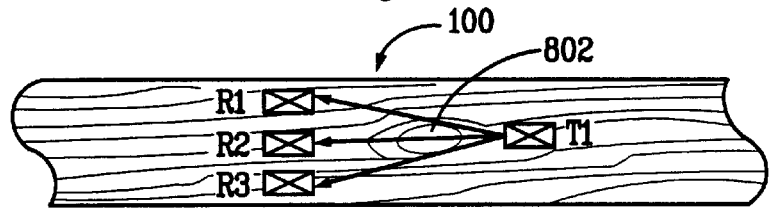
FIG. 9 shows the interposition of a knot or other defect in the path of the ultrasound wave.

In addition to grain angle determination, it is possible to perform defect detection for defects such as knots or decay, with the same transducer orientation, as shown in FIG. 9. The ultrasound wave that travels on a path through the defect region 802 is substantially altered, and undergoes significant attenuation and distortion. This is because the knot 802 is a region of perpendicular grain orientation, and the region around the knot 802 also has significant grain distortion.

Figure 10:
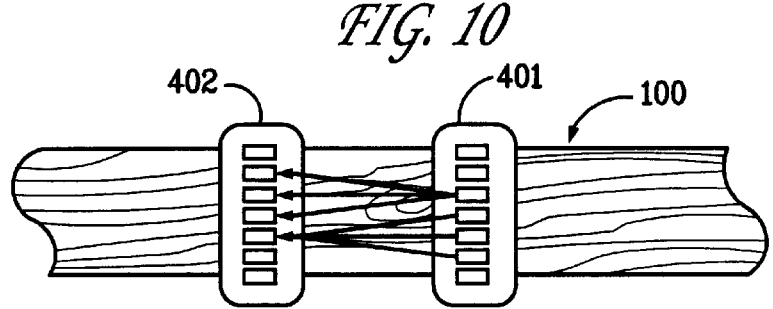
FIG. 10 shows an embodiment of the invention including a multiplicity of ultrasound transmitters and receivers contained within two rollers for detecting relative transmission values.

Similarly, a single receiver can receive signals from several transmit transducers, although the transmitters must be properly timed to avoid ambiguity. This embodiment is shown in FIG. 10. Here, multiple transmitter elements 401 and multiple receiver elements 402 are placed within single rollers, as described in U.S. Provisional Patent Application No. 60/133,015. The approach shown in FIG. 10 permits additional wave motion directions, so that the same area of the wooden member 100 is interrogated with several transmitter/receiver pairs, at different angles, increasing the resolution of the defects, and improving the statistical confidence of any single measurement.

Figure 11:
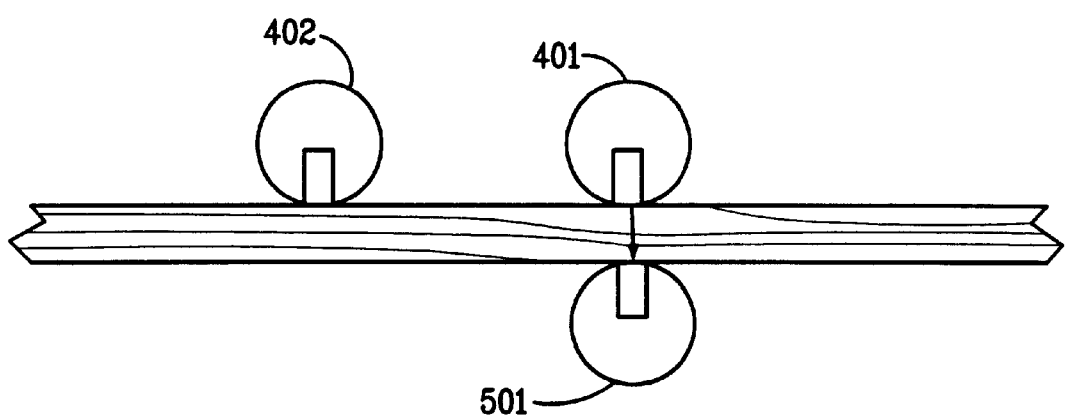
FIG. 11 shows an additional embodiment of the invention further including an array of ultrasound transducers on the opposite side of the wooden member from the transmitter.

Finally, FIG. 11 shows the addition of a second set of receiving transducers 501 located on the opposite side of the transmitter 401. The utility of using arrays of transmitter/receiver pairs situated on opposite sides of the wooden member 100 were described in U.S. patent application Ser.

No. 09/522,642, filed on Mar. 10, 2000, and pending in the United States Patent and Trademark Office, and U.S. Pat. No. 6,029,522, granted on Feb. 29, 2000 to Schafer et al. When used in combination with the method disclosed herein, the embodiment of FIG. 11 allows at least three separate sound velocities to be measured at the same time, with a single transmit wave, including longitudinal and shear wave components at receiver element 402 and longitudinal wave components at transducer 501. Variations in the measured signals may then be measured and processed to determine grain angle, the presence of abnormalities in the wood, and the like, through comparison to standard wooden elements, relative comparisons of multiple measurements (as in the embodiment of FIG. 10), and the like. Because only one transmit waveform is required and not two or three, the motion of the wooden member may be increased for a given resolution along the wooden member. This is because the limiting factor in ultrasound scanning of these materials is the time required for the wave to propagate from transmitter to receiver. Firing multiple waveforms, or firing waveforms too quickly, can lead to ambiguity at the receiver, because it is not possible to distinguish one wave from another. The present invention avoids this problem.

The combination method shown in FIG. 11 also permits additional defect detection capabilities, both in terms of resolution and confidence in the results. This is because the two sets of data complement each other, such that defects can be resolved with better resolution and confidence. Note, for example, a knot that completely passes from one side (top) to the other (bottom) of the wooden member. It may be first detected because of a reduction in time-of-flight (increased sound velocity) between transducers oriented on the top and bottom. This is because the orientation of the grain angle of the knot is from top to bottom (at right angles to the rest of the wooden member). As the wooden member 100 is transported in the longitudinal direction, the knot would be positioned between the two sets of transducers 401 and 402 mounted on the top surface. The knot would then be detected by a decrease in amplitude of the signal travelling between these rollers. This would confirm the measurement data taken through the member. This is an important improvement over the prior art, which generally relied on a single measurement direction (e.g. measurement of sound speed through the board to detect knots and other defects).

Thus, the technique of the invention relies on the ultrasound propagation properties of the wooden member, whereas two of the prior art solutions use either mechanical bending or X-rays. These prior art solutions provide either limited, albeit direct strength data (mechanical bending), or high resolution density data (X-ray) which is only weakly indicative of strength. On the other hand, the third solution mentioned (Rajeshwar et al) uses ultrasound from the sides of the wooden member, and is primarily concerned with detection of edge knots, which are, in fact, a strength limiting defect. In contrast, the present invention provides sophisticated signal processing and transducer fabrication technologies that have provided unique capabilities. This technique has allowed the inventors to generate detailed acoustic signature data, which few others have had in the past.

Experimental Data

The present inventors have successfully demonstrated the generation of separate waveforms using a transmit/receive pair on one side of the wooden member, which were shown to relate to both the longitudinal and shear modes of ultrasound wave propagation. The present inventors also successfully demonstrated the detection of decay, knot, and other conditions affecting structural properties by the reduction in signal strength of the ultrasound waveforms between a transmitter and receiver pair on the same side of the wooden member, when such defect was positioned between the rollers.

As an example, a series of tests were performed on Southern pine sapwood specimens, 20" long, 1.5"×1.5" wide. These specimens were placed in the ground for periods of time ranging up to 48 months, in order to induce different levels of decay. After retrieval from the ground, they were tested using ultrasound transducers spaced 4" apart on one side only, with 1.25 MHz center frequency. After the ultrasound measurements, the specimens were tested in compression, parallel to the grain, with full lateral support during compression (to avoid rupture). Part of the resultant data is shown in the table below, showing the change in Insertion Loss as a function of compression strength, using the unexposed control as the standard (0 dB).

| Maximum Compressive Load (kpsi) | Insertion Loss relative to control (dB) |
| --- | --- |
| 14,972 | 0.0 |
| 9,975 | −0.9 |
| 8,662 | −4.7 |
| 8,775 | −2.8 |
| 6,575 | −9.8 |

Those skilled in the art will appreciate that not only was the Insertion Loss indicative of loss of strength, but other parameters, such as time of flight, did not change until the later stages of decay. This indicates that a multi-parameter approach would be able to better gauge decay (strength) than single parameter measurements.

In another test, the Insertion Loss was measured as a function of wood fiber angle using a Douglas fir board, with a 3 inch separation between transmitter and receiver. The pair was placed on the board surface, and the axis between them was positioned relative to the orientation of the wood fiber. Data were taken at 0°, 8°, 15° and 90°, with 0° being parallel to the wood fiber orientation. The results are shown in the table below:

| Angle | Insertion Loss re 0° |
| --- | --- |
| 0° | 0 |
| 8° | −8 |
| 15° | −10 |
| 90° | −13 |

This indicates that the energy transmission using this method is very sensitive to wood fiber (grain angle) orientation.

In general, it is possible using the techniques of the invention to generate a multivariate regression formula to indicate the relative strength of a wooden member using a formula of the type:

$$\text{Ultimate Tensile Stress or Ultimate Compressive Stress} = \left(\frac{C_\parallel}{C_\perp}\right)^X \left(\frac{\text{Attenuation}_\parallel}{\text{Attenuation}_\perp}\right)^Y$$

where the subscripts $\parallel$ and $\perp$ indicate parameters measured parallel and perpendicular to the grain. The technique disclosed herein would thus be able to measure all parameters with a single measurement arrangement. Those skilled in the art will appreciate that the present invention provides a significant increase in resolution, as well as providing data with fewer roller units than the prior art system described above. For example, the solution proposed by Rajeshwary et al. required up to six rollers with single transducers, while the present invention requires only three rollers with multiple transducers in each roller.

It also will be appreciated by those skilled in the art that the foregoing has set forth an illustrative embodiment of the invention but that numerous alternative embodiments are possible without departing from the novel teachings of the invention. Accordingly, all such modifications are intended to be included within the scope of the appended claims.

We claim:

1. A method of detecting anomalies and/or grain variations in a wooden member, comprising the steps of:
    at least one ultrasonic transmitter applying an ultrasound waveform into a surface of said wooden member so as to generate a multiplicity of ultrasonic waves;
    measuring at at least one ultrasonic receiver disposed on a surface of said wooden member longitudinal and shear ultrasonic wave components of said multiplicity of ultrasonic waves that have traveled along different paths through said wooden member; and
    measuring variations in said longitudinal and shear ultrasonic wave components of said multiplicity of ultrasonic waves at said at least one receiver as representative of said anomalies and/or grain variations in said wooden member at positions of said wooden member between said ultrasonic transmitter and said at least one ultrasonic receiver.

2. A method as in claim 1, wherein said variations measuring step comprises the step of comparing the longitudinal and shear ultrasonic wave components along said different paths to determine grain angle of said wooden member.

3. A method as in claim 2, wherein said variations measuring step comprises the step of comparing measured longitudinal and shear ultrasonic wave values taken along said different paths to each other to determine said variations.

4. A method as in claim 2, wherein said variations measuring step comprises the step of comparing measured longitudinal and shear ultrasonic wave values to references values taken from a normalized wooden member to determine said variations.

5. A system which detects anomalies and/or grain variations in a wooden member, comprising:
    at least one ultrasonic transmitter adapted to apply an ultrasound waveform into a surface of said wooden member so as to generate a multiplicity of ultrasonic waves;
    at least one ultrasonic receiver disposed on a surface of said wooden member so as to receive said multiplicity of ultrasonic waves after propagation of said ultrasonic waves through said wooden member; and
    processing apparatus which measures longitudinal and shear ultrasonic wave components of said multiplicity of ultrasonic waves that have traveled along different paths through said wooden member to at least one receiver so as to identify said anomalies and/or grain variations in said wooden member.

6. A system as in claim 5, wherein said at least one ultrasonic transmitter and said at least one ultrasonic receiver in communication with each other are located in a spaced relation along the same surface of said wooden member.

7. A system as in claim 5, wherein said at least one ultrasonic transmitter comprises a plurality of ultrasonic transmitters in a first roller adapted to roll along said surface of said wooden member and said at least one ultrasonic receiver comprises a plurality of ultrasonic receivers in a second roller adapted to roll along said surface of said wooden member.

8. A system as in claim 5, wherein said at least one ultrasonic receiver comprises a first ultrasonic receiver disposed a predetermined distance from said at least one ultrasonic transmitter along said surface of said wooden member and a second ultrasonic receiver disposed on an opposite surface from said surface of said wooden member at a position substantially opposite said at least one transmitter.

9. A system as in claim 8, wherein said first ultrasonic receiver receives a longitudinal ultrasonic wave and a shear ultrasonic wave and said second ultrasonic receiver receives said longitudinal ultrasonic wave, and said processing apparatus determines variations in the longitudinal ultrasonic wave and the shear ultrasonic wave detected by said first and second ultrasonic receivers.

* * * * *